(12) United States Patent
Hylands et al.

(10) Patent No.: US 6,806,090 B1
(45) Date of Patent: Oct. 19, 2004

(54) PROCESS FOR QUALITY CONTROL AND STANDARDIZATION OF MEDICINAL PLANT PRODUCTS

(75) Inventors: Peter John Hylands, Oxford (GB); Jeremy Kirk Nicholson, London (GB); Elaine Holmes, London (GB); Michael John Dunn, Surrey (GB)

(73) Assignee: Oxford Natural Products PLC, Oxford (GB)

( * ) Notice: Subject to any disclaimer, the term of this patent is extended or adjusted under 35 U.S.C. 154(b) by 0 days.

(21) Appl. No.: 09/890,973

(22) PCT Filed: Feb. 10, 2000

(86) PCT No.: PCT/GB00/00428

§ 371 (c)(1),
(2), (4) Date: Sep. 21, 2001

(87) PCT Pub. No.: WO00/47992

PCT Pub. Date: Aug. 17, 2000

(30) Foreign Application Priority Data

| Feb. 10, 1999 | (GB) | ............................................. 9903011 |
| Aug. 18, 1999 | (GB) | ............................................. 9919573 |
| Dec. 2, 1999 | (GB) | ............................................. 9928541 |

(51) Int. Cl.$^7$ .............................................. G01N 33/00
(52) U.S. Cl. ........................................ 436/86; 436/173
(58) Field of Search ................ 436/173, 86; 435/40.51; 324/309

(56) References Cited

FOREIGN PATENT DOCUMENTS

| EP | 0 099 810 | 2/1984 |
| WO | WO96/18911 | 6/1996 |

OTHER PUBLICATIONS

Cooke R J: "Gel electrophoresis for the identification of plant varieties" Journal of Chromatography A, NL, Elsevier Science, vol. 698, No. 1, Apr. 28, 1995, pp. 281–299.

Kowalski B R et al: "Pattern Recognition. A Powerful Approach Chemical Data" Journal of the American Chemical Society, US, American Chemical Society, Washington, DC, vol. 94, No. 16, Aug. 9, 1972 (Aug. 9, 1972), pp. 5632–5639.

Database Biosis Online! Biosciences Information Service, Philadelphia, PA, US PREV199799476639, 1997 Perry, Nigel B., et al: "Alkamide levels in Echinacea purpurea: a rapid analytical method revealing differences among roots, rhizomes, stems, leaves and flowers."

Database Biosis Online! Biosciences Information Service, Philadelphia, PA, US PREV199800038614, 1998 Barakat; Heba H., et al.: "Polyphenolic metabolites of Epilobium hirsutum".

*Primary Examiner*—Yelena G. Gakh
(74) *Attorney, Agent, or Firm*—Nixon & Vanderhye P.C.

(57) ABSTRACT

A process for establishing a standard specification for a medicinal plant material comprises: (i) preparing a test solution or test extract of a sample of the medicinal plant material which is known to possess the or each property required for the standard; (ii) submitting the said solution or extract to two or more analytical methods including (a) a combination of NMR spectroscopy and a computer-based pattern recognition technique, and (b) one or more biological profiling techniques; (iii) obtaining results from the analytical methods used in step (ii); and (iv) establishing a standard specification for the said plant material on the basis of the results obtained in step (iii). Candidate samples of the medicinal plant material may subsequently be tested for compliance with the standard. They can be accepted or rejected depending on whether they give analytical results which fall within or outside either part or all of the specification established in step (iv). This approach to standardization and quality control is particularly applicable to mixtures of medicinal plant materials.

14 Claims, 7 Drawing Sheets

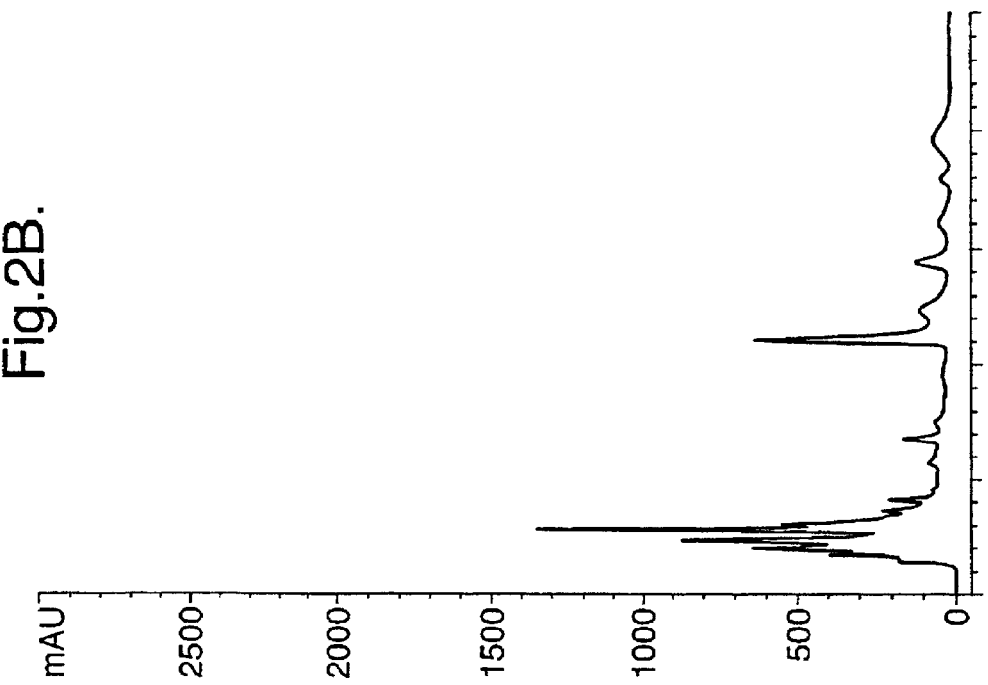
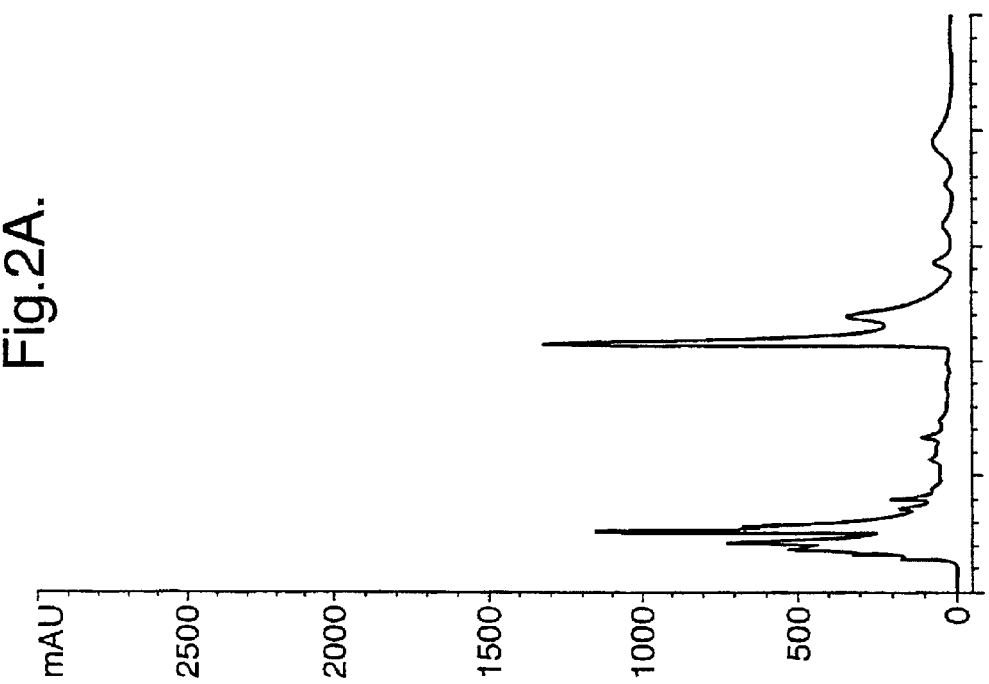

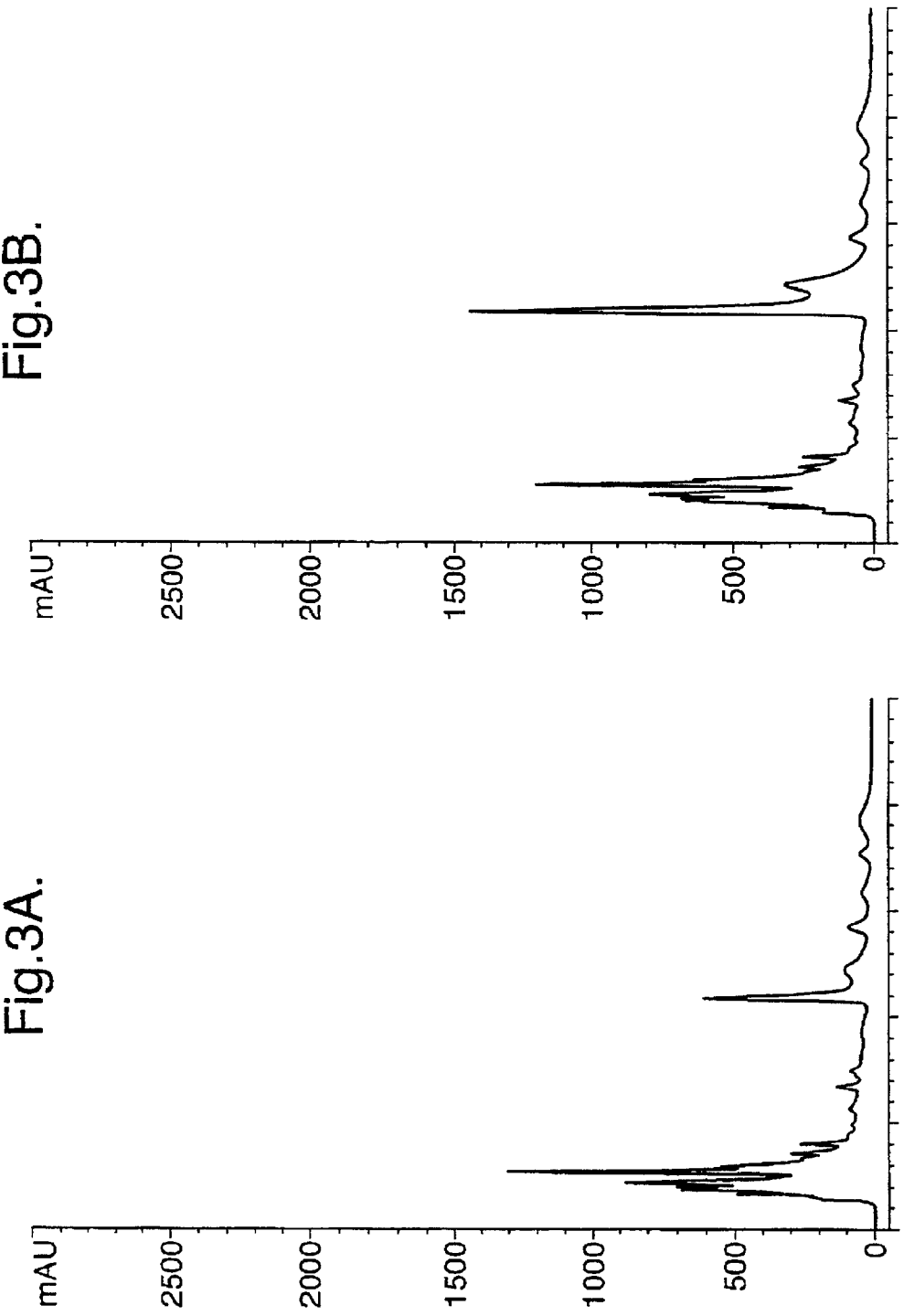

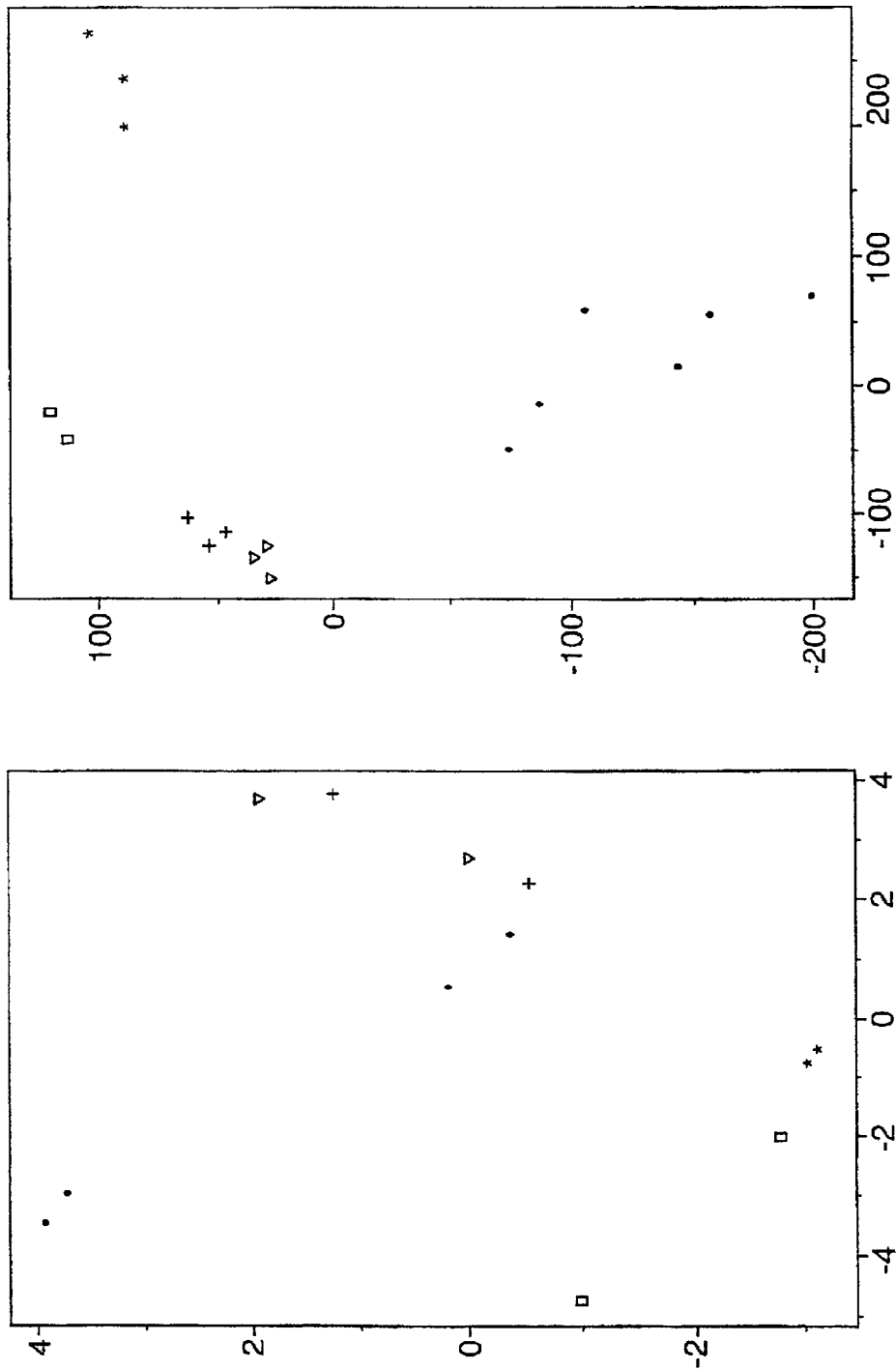

PROCESS FOR QUALITY CONTROL AND STANDARDIZATION OF MEDICINAL PLANT PRODUCTS

The present invention relates to the use of NMR spectroscopy and biological profiling, in combination with computer-based statistical procedures, in the standardisation and quality control of medicinal plant materials.

Many societies around the world have developed, through the centuries, a system of traditional medicine relying largely on the use of plants and herbs as therapeutic substances. As used herein, the term "plant" encompasses plants, including herbs, and fungi.

In recent years there has been a significant growth of interest amongst the general public in the direct use of plants and plant extracts as health modifying agents, for instance *Panax ginseng*, *Allium sativum* (garlic), *Ginkgo biloba*, *Hypericum perforatum* (St John's wort), *Echinacea angustifolia* and *Aloe vera*. These are currently available on the market as herbal products and dietary supplements and annual sales of these products worldwide currently run to tens of billions of dollars. In spite of this marketing potential the mainstream pharmaceutical industry has not so far directed its attention to the development of medicinal products derived from plants. This is due in part to problems associated with the complex nature and inherent non-uniformity of plant materials, including the lack of an established system by which drug regulatory approval for such products can be secured.

The materials used in herbal and plant based medicine are usually whole plants, parts of plants or extracts of plants or fungi. Since plant and fungal materials contain many different chemical components the materials are, by definition, complex mixtures. This makes it very difficult to standardize and control the quality of the materials. Many of the remedies employed in traditional Chinese medicine and Ayurvedic medicine mentioned above are mixtures of two or more plant-based components. They are therefore effectively mixtures of mixtures and thus even more difficult to analyse than herbal remedies based on a single plant material. Furthermore, the recipes and methods of manufacture used for such remedies frequently remain undisclosed. These factors make it very difficult to ensure that two samples of a given remedy, obtained from disparate sources and ostensibly identical, do in fact contain the same mixture of ingredients. This problem, which leads to difficulties in controlling the quality of such materials, has so far limited the acceptability of Eastern herbal remedies to Western herbal practitioners.

The plants used in the practice of herbal medicine are frequently unavailable locally and therefore need to be obtained from sources which are remote from the end user. However, the supply of such plants from remote locations can be erratic and inaccurate, particularly because no detailed monographs including identity and quality standards exist for many such plants. The complex mixture of ingredients found in medicinal plants will in any event vary widely in type and concentration depending on many factors including the botanical origin, the location where the plant is grown, the time of year when the plant is harvested, the conditions under which the material is stored and processed and the extraction procedure used. When these plants are in turn mixed with other plants, for instance according to traditional Chinese herbal recipes, there is considerable scope for variability in the resulting product.

It is virtually impossible at present to provide any assurance that samples of a given plant material obtained from disparate sources will possess a uniform identity and biological activity. The present invention addresses this problem by providing a means of standardising a medicinal plant material. The approach takes account of the totality of the components of the plant material without demanding any inquiry into the intrinsic nature of either the components themselves or the plant's biochemistry. It involves interrogating the consistency of a plant material on both a chemical level and a biological level.

Thus the process of the present invention provides a means of defining a standard for a given medicinal plant material on the basis of a known sample of the material which possesses the particular property desired for the standard. A specification for the standard is established by submitting the known sample to (a) a combination of NMR spectroscopy and a computer-based pattern recognition technique and (b) one or more biological profiling techniques, and defining the results thus obtained as the standard specification. Subsequent "candidate" samples of the said plant material can then be tested for compliance with the standard. They can be accepted or rejected depending on whether they give analytical results which fall within or outside either part or all of the established specification.

The present invention accordingly provides a process for establishing a standard specification for a medicinal plant material, the process comprising:

(i) preparing a test solution or test extract of a sample of the medicinal plant material which is known to possess the or each property desired for the standard;

(ii) submitting the said solution or extract to two or more analytical methods including (a) a combination of NMR spectroscopy and a computer-based pattern recognition technique, and (b) one or more biological profiling techniques;

(iii) obtaining results from the analytical methods used in step (ii); and (iv) defining a standard specification for the said plant material on the basis of the results obtained in step (iii).

The standard specification resulting from step (iv) is thus based on the results of NMR spectroscopy and computer-based pattern recognition as well as on the results of one or more biological profiling techniques. However, when candidate samples of the medicinal plant material are tested for compliance with the standard they need not all be submitted to both the NMR spectroscopic analysis and the biological profiling. Rather, all candidate samples are submitted to NMR spectroscopy and pattern recognition whilst only selected candidate samples, for instance taken periodically from batches of the medicinal plant material, are tested for compliance with the biological profiling aspect of the standard specification. The purpose of this is to rely principally on the analytical method which is best suited to convenient and fast operation on a high-throughput scale. This is the NMR spectroscopic and pattern recognition analysis. The biological techniques are typically used on a random basis for validation and reinforcement of the decisions being made to accept or reject the candidate samples on the basis of the NMR spectroscopic and pattern recognition results.

Accordingly the invention further provides a process for providing a sample of a medicinal plant material, which sample complies with a previously defined standard specification for that plant material, the process comprising:

(i') preparing a test solution or test extract of a candidate sample of the medicinal plant material;

(ii') submitting the said solution or extract to analysis by a combination of NMR spectroscopy and a computer-based pattern recognition technique;

(iii') obtaining results from the analysis of step (ii'); and (iv') selecting the candidate sample if the results obtained in step (iii') comply with the standard specification for the said material established in step (iv) of the process above.

This process is conveniently carried out on a high-throughput batch scale. Candidate samples are taken from batches of the same plant material and submitted to steps (i') to (iv'). When the candidate sample is selected for submission to biological profiling in addition to the NMR spectroscopic and pattern recognition analysis the above step (iv') is replaced by the following steps:

(iv'a) submitting the solution or extract prepared in step (i') to one or more biological profiling techniques;

(iv'b) obtaining results from the or each technique used in step (iv'a); and (iv'c) selecting the candidate sample if the results obtained in steps (iii') and (iv'b) comply with the standard specification for the said material as established in step (iv) of the process above.

The biological profiling techniques are discussed in more detail later on.

The "property desired for the standard" in the context of the present invention may be any property or quality possessed by, or attributed to, a medicinal plant material. Examples of this include a clinically proven therapeutic efficacy, a pharmaceutical grade quality, a particular variety of a given plant genus, an authenticated origin (in terms of either growth location or commercial batch) and a particular pathological state. The pathological state in question may be a given level of maturity, dictated for instance by the time of harvesting, or an established resistance to a parasite, herbicide, insecticide or other agent with potential for damage to the plant in question.

In a preferred aspect of the invention the sample of medicinal plant material which is "known to possess the or each property desired for the standard" is a sample of authenticated and audited plant material of which the provenance is known. A standard specification is established by submitting that sample to NMR spectroscopy/pattern recognition and biological profiling as described above. Subsequent samples of the same plant material, the origin or quality of which is not known or is in doubt, can then be tested for compliance with the standard specification thus established for the authenticated and audited material.

Nuclear magnetic resonance spectroscopy (NMR) is known by itself as an analytical tool in the investigation of plant materials. One example of its application is in the verification of the authenticity of drinks derived from fruit. In one approach hydrogen-2 NMR spectroscopy has been employed with the technique of site-specific natural isotope fractionation (SNIF-NMR) as a means of establishing the authenticity of fruit juices. For instance, in JAOAC Int. 1996 July–August, 79(4): 917–928 Martin et al describe the use of hydrogen-2 NMR spectroscopy (SNIF-NMR method) to detect fruit juices which have been adulterated with added beet sugar. The technique relies on the fact that, when a fruit juice or fruit concentrate is fermented, the proportion of the resulting ethanol molecules which are mono-deuterated on the methyl site decreases with the addition of beet sugar. Thus any fruit juice sample to which beet sugar has been added will have a significantly lower (D/H) isotope ratio than a corresponding authentic sample. This technique has also been applied to the detection of wine chaptalisation using hydrogen-2 NMR spectroscopy, as reported for example in J.Chim. Phys.-Chim Biol. 1983, vol 80, pp 293–297 by Martin et al.

Hydrogen-1 NMR spectroscopy cannot itself conveniently be applied to plant materials because it generates spectra that are too complicated to be analysed visually. A solution to this problem, reported for instance by Kowalski and Bender in J. Am. Chem. Soc. 1972, 94, 5632–5639, is to analyse the data by appropriate multivariate statistical analysis, for example principal component analysis (PCA). This is a technique of pattern recognition where the dimensionality of the data is reduced by combining correlated variables (peaks in the spectrum) to form a new smaller set of independent orthogonal variables called principal components (PCs). These PCs are ordered according to their ability to explain the variance contained in the original data. A projection of the samples into a space spanned by the first PCs provides an insight into the similarity or dissimilarity of the samples with respect to their biochemical composition. Unknown or test samples can also be projected onto this space and can thus often visually be compared with the reference samples (Vogels et al, J. Agric. Food Chem. 44,175–180, 1996).

The combination of hydrogen-1 NMR spectroscopy with pattern recognition techniques has been applied as a screening tool in determining the authenticity of orange juice (Vogels et al, 1996 loc. cit.). The adulteration of suspect samples could be detected by this means. The identity of the responsible contaminants was then determined by correlation of the PCA results with particular resonances present in the original NMR spectrum.

A combination of hydrogen-1 NMR spectroscopy and carbon-13 NMR spectroscopy with PCA has also been used to differentiate wines on the basis of their origin (Vogels et al, Chemometrics and Intelligent Laboratory Systems: Laboratory Information Management, 21 (1993) 249–258). Discriminant plots of samples originating from different wine-producing regions in Germany showed clustering of the samples by origin in the discriminant space after a supervised method of statistical analysis. Subsequently, reconstructed spectra were prepared from the PCA data to reveal the NMR spectroscopic peaks of the particular wine constituents (for instance monosaccharides such as glucose, mannose, rhamnose and galactose) responsible for the differentiation. Similar studies are reported elsewhere, for instance by Vogels et al in Trends in Flavour Research, Maarse & Van de Heij (Eds), Elsevier, Amsterdam (1994) pp 99–106.

Another application of hydrogen-1 NMR spectroscopy and principal component analysis is reported by Trevisan et al in Chapter 8 of "Characterisation of cell suspension cultures of hop, *Humulus lupulus* L.", a thesis presented to the University of Leiden, the Netherlands, pages 95–122, published in 1997. The authors carried out hydrogen-1 NMR spectroscopy and PCA on treated cell extracts with the aim of identifying specific metabolites accumulated by the cells following treatment. They were therefore interested in following specific peaks in the NMR spectrum which were known to be due to individual cell components.

In contrast to these reported methods the NMR spectroscopic and pattern recognition procedure employed in the process of the present invention requires neither an investigation into the biochemistry of the plant being analysed nor a subsequent correlation of the pattern recognition results with particular NMR spectroscopic resonances attributed to specific component(s) of the plant material. Instead it relies upon the information presented by the inherent pattern of clusters derived from NMR data, those data in turn reflecting the totality of the compounds in the plant material which respond to the NMR spectroscopic technique being used.

The NMR spectroscopy combined with computer-based pattern recognition (hereinafter termed NMR spectroscopy/pattern recognition) employed in the process of the invention typically comprises:

(a) submitting the test solution or test extract to NMR spectroscopy and recording one or more NMR spectra; and (b) submitting the data obtained from the or each NMR spectrum to a multivariate analysis to generate one or more points on a score plot.

A sphere of acceptability is typically defined around the point or points on the score plot generated in step (ii) above when the NMR spectroscopy/pattern recognition analysis is being used to establish a standard specification for a medicinal plant material. That sphere then constitutes part of the specification. Candidate samples of the same material are subsequently accepted or rejected depending whether, when submitted to the NMR spectroscopy/pattern recognition analysis defined above, they give points in step (ii) which fall within or outside the sphere.

The NMR spectroscopy/pattern recognition can be used by itself as a way of standardising samples of medicinal plant materials. Accordingly, in one aspect the present invention provides a process for providing a sample of a medicinal plant material which complies with a previously established standard specification for that material, the process comprising:

(i") preparing a test solution or test extract of a candidate sample of the said plant material;

(ii") submitting the test solution or test extract to NMR spectroscopy and recording one or more NMR spectra;

(iii") submitting the data obtained from the or each said NMR spectrum to a multivariate analysis to generate one or more points on a score plot; and (iv") selecting the candidate sample as a sample which complies with the said standard specification only if the points generated on the score plot in step (iii) fall within a sphere of acceptability as defined in the standard specification.

The standard specification in this aspect of the invention may be provided by a process which comprises:

(i'") preparing a test solution or test extract of a sample of the said plant material which is known to possess the or each property desired for the standard;

(ii'") submitting the test solution or test extract to NMR spectroscopy and recording one or more spectra;

(iii'") submitting the data obtained from the or each said NMR spectrum to a computer-based multi-variate analysis to generate one or more points on a score plot; and (iv'") defining a sphere of acceptability around the points generated in step (iii'") as the, or as part of the, standard specification for the said plant material.

In general multivariate analysis theory, the total data is the product of the scores multiplied by the loadings. The loadings plot can be used to define the contribution of each of the variables (spectral descriptors). A "score plot" is a graphic representation in which samples are projected into the space spanned by two or more principal component axes. Principal component analysis (PCA) is a particular method used to analyse data included in a multivariate analysis. In PCA the position of the samples can be plotted in a score plot in two dimensions where similar samples will tend to form clusters while dissimilar samples will tend to spread over large distances (Kowalski & Bender, 1972, loc. cit. and Trevisan, 1997, loc. cit.).

The context in which the points are generated on the score plot in the process of the present invention must be the same when establishing the standard specification as when analysing candidate samples for compliance with the standard. The components of the methodology used to establish the positioning of the point or points on the score plot for the known sample used to define the standard must be present when the NMR spectroscopic data from the candidate test samples are processed. In practice the data derived from the NMR spectrum of the sample used as the standard are subjected to appropriate manipulation by multivariate statistical methods, for example principal component analysis or canonical variation, together with those of the standard. The sphere of acceptability is defined by limits in the score plot which have been established on the basis of the position in the score plot of points derived from one or more extracts of the known sample. In a preferred aspect of the invention the multivariate analysis is performed using an unsupervised methodology.

The NMR spectroscopic technique used in the invention may involve carrying out hydrogen-1 NMR spectroscopy at high fields in combination with multivariate analysis. In this particular aspect the NMR spectra are typically measured at 400 to 700 MHz. The data derived from them are then analysed by multivariate analysis software, for instance the commercially available "Pirouette" package.

Examples of the high resolution hydrogen-1 NMR spectroscopic and pattern recognition analysis are discussed by M. L. Anthony et al in Biomarkers 1996, 1, 35–43 and Molecular Pharmacology 46, 199–211, 1994, and by J. O. T. Gibb et al in Comp. Biochem. Physiol. vol. 118B No. 3, pp 587–598, 1997.

As an alternative to 1-dimensional high field hydrogen-1 NMR spectroscopy, 1-dimensional NMR spectroscopy using other NMR-active nuclei such as carbon-13 or hydrogen-2 may be used in the present invention. It is also possible to use a range of 2-dimensional pulse sequence spectroscopic investigations with hydrogen-1 or other NMR-active nuclei such as those mentioned above. The same principles apply in each case, though, and the results are analysed by appropriate multivariate analysis.

The NMR spectra may be normalised or non-normalised before the computer-based pattern recognition is carried out. Normalisation has the effect of removing peak intensity, which is a purely quantitative parameter of the spectra, as a discriminating factor. Normalisation is therefore typically carried out when the main objective of the procedure is to highlight qualitative differences between spectra obtained from different samples. However, in some cases peak intensity may be required as a discriminating factor when absolute quantitative values, for instance potency, are required. In such situations the spectra are non-normalised.

An important advantage of NMR spectroscopy/pattern recognition is that it is not limited by a selective delivery or detection system. Spectra can be recorded without prior purification of the test solution or test extract, thus allowing all components of the sample which possess a proton to contribute to the overall NMR spectrum. Analysis of the spectrum by the multivariate analytical techniques discussed above reveals potential valuable discriminating features of the spectra which can be used with a high degree of precision for the description of the complex mixtures of components contained in plant materials.

It is nonetheless possible in certain cases for the differentiation of samples of plant material on the score plot to be poor, with points deriving from identical samples of a given plant material being spread widely rather than forming a cluster. This loss of similarity arises when there is variation in the NMR spectroscopic shift values of individual components of the plant material. Such variation may be caused, for instance, by the presence of an overwhelmingly high concentration of one particular compound in the plant material or by the modifying effect of pH or metal ions which cause shift values to change. If this problem occurs the test solutions or test extracts of the plant material which are submitted to NMR spectroscopy may be pre-treated to remove the source of error and achieve better clustering in the score plot. In one aspect the process of the invention therefore includes the additional initial step of purifying the test solution or test extract of the candidate sample of plant material prior to submitting it to NMR spectroscopy.

Tea provides a convenient illustration of this principle. Signals due to caffeine dominate the hydrogen-1 NMR spectrum of tea and so when NMR spectroscopic results of tea are processed by multivariate analysis the points on the score plot for samples of the same tea do not form clusters. If caffeine is removed from tea prior to carrying out NMR spectroscopy, for instance by reverse phase chromatography, proper clustering of the samples occurs and the similarities between like samples on the score plot become clear. This is illustrated in Example 2 and accompanying FIGS. 4A and 4B. FIG. 4A is a score plot for untreated tea samples where clustering is indistinct. FIG. 4B is a score plot for pre-treated tea where, in contrast, there is clear clustering which allows positive discrimination.

The NMR spectroscopy/pattern recognition analysis is highly sensitive and has the capacity to differentiate samples of plant material which appear to be identical when analysed by other methodologies. This has again been illustrated using tea. Comparative Example 1 describes the analysis by high performance liquid chromatography (HPLC) of extracts of two different types of tea. The resulting chromatograms are shown in accompanying FIGS. 2 and 3. One experiment used untreated samples (chromatogram A in each of FIGS. 2 and 3) and the other used a treated sample (chromatogram B in each Figure).

The Figures show first of all that HPLC does not clearly distinguish between treated and untreated samples of tea since chromatograms 2A and 2B are virtually identical, as are chromatograms 3A and 3B. Second, the Figures show that HPLC does not have the power to discriminate between different types of tea since the chromatograms of FIG. 2 are virtually identical to those of FIG. 3. In both these respects HPLC contrasts with the NMR spectroscopy/pattern recognition technique used in the present invention as illustrated in Example 2 and the accompanying FIGS. 4A and 4B.

An important application of the process of the present invention is in the standardisation of mixtures of plant materials. Examples of such mixtures include remedies from Traditional Chinese Medicine as discussed above. These are typically mixtures of several different plants and fungi prepared in accordance with recipes that may be many hundreds of years old. To date there has been no analytical technique by which producers of such materials could reliably and consistently differentiate their products from ostensibly identical products sold by competitors under the same name. It has now surprisingly been found that the NMR spectroscopy/pattern recognition technique used in the present invention can provide clear differentiation between samples of a given mixture of plant materials which are supposed to be identical but are obtained from different sources. This is illustrated in Example 5 and accompanying FIG. 7. The process of the invention therefore allows mixtures of plant materials to be differentiated and standardised.

The combination of NMR spectroscopy/pattern recognition and biological profiling is frequently desirable since the complex mixture of compounds in a medicinal plant material may show an overall clinical effect which may derive principally from one particular component but which is considerably modified or potentiated by the presence of other components. Biological profiling can thus provide a quantifiable measure of the biological effects of plants and plant extracts, thereby complementing and/or confirming the information obtained by the NMR spectroscopic and pattern recognition analysis.

The biological profiling techniques used in the process of the invention contribute a means of quality controlling and standardising a desired sample of plant material in terms of its biological activity. It is now recognised that the overall efficacy of plant based medicines does not solely derive from a single active component but is due also to auxiliary compounds which are present in the complex mixture of substances in the plant. The biological profiling techniques used in the process of the invention allow synergistic effects exerted by these auxiliary compounds to be studied without the need to identify the compounds themselves. he synergistic effects which may be observed include, for instance, potentiation of the activity of the principal component, enhancement of the selectivity or bioavailability of the therapeutic substance and suppression of unwanted side effects. This aspect of the biological profiling is particularly useful for substantiating the claim that the use of a whole plant or plant extract in therapy is more beneficial than the use of single components isolated from the plant.

A preferred biological profiling technique is protein analysis, particularly proteomics. This is because changes in protein expression represent the ultimate biological effect irrespective of the particular mechanism of action such as enzyme inhibition, receptor binding inhibition or signal transduction modulation. The term proteome describes the complete set of proteins that is expressed, and modified following expression, by the entire genome in the lifetime of a cell. Proteomics is the study of the proteome using technologies of large-scale protein separation and identification (Nature, vol 402, 1999, p.715). A proteomics analysis is illustrated in Example 6 which follows.

Accordingly, in a preferred aspect of the present invention the biological profiling technique comprises:

(i) providing a target cell selected according to the clinical indication in which the medicinal plant material is active and incubating the target cells with a candidate sample of the said material; and (ii) subjecting the incubated cells to gel electrophoresis on a 2-D gel and observing the change in protein expression in the cells as a result of exposure to the test sample.

In the process of the invention the above steps (i) and (ii) are carried out on a sample of the plant material which possesses the or each property desired for the standard. The overall pattern of change in protein expression observed in step (ii) is defined as part of the standard specification for that plant material. Candidate samples of the same plant material may then be accepted or rejected depending whether they give the same pattern when submitted to the above steps (i) and (ii).

An appropriate target cell is selected in the first step according to the clinical indication, or disease, which it is desired to model. Following incubation of the cell with the test sample, the proteins in the target cell are separated into individual proteins by two dimensional electrophoresis. Detection and analysis of the resulting protein patterns is typically undertaken using computerized image analysis techniques, and proteins are identified using microsequencing and mass spectroscopy. The results may, if desired, be submitted to computer-based pattern recognition procedures such as principal component analysis, as described above. Changes in protein expression which are detected following incubation of the target cell with the test sample are then compared with the corresponding changes detected following incubation of the target cell with a known sample which has already been shown to possess activity against the clinical indication in question.

The potency of the test sample can be related to the potency of a pharmaceutical grade standard by comparing the concentration of the test sample necessary to produce the response of the standard.

A further biological profiling technique is a receptor binding or enzyme inhibition assay. This can give a quantifiable measure of the biological activity of a plant material. Such an assay may be conducted in accordance with a conventional assay protocol. One example of a suitable assay is a method for screening a plant material as a candidate for the treatment or prophylaxis of cancer or inflammation, the method comprising determining whether the substance suppresses the stimulation of a gene promoter which has been implicated in carcinogenesis or inflammation.

In the process of the invention the plant material typically consists of, or is derived from, a whole plant, a part of a plant, a plant extract or a plant fraction. Preferably the material consists of, or is derived from, one or more of the roots, leaves, buds, flowers, fruit, juice and seeds of a plant.

The inherent variability of plant materials presents a particular problem to the drug regulatory authorities who need to be convinced that a candidate product for pharmaceutical licencing is of a consistent and verifiable quality. The reason for this is that the effectiveness of dosage levels and treatment protocols need to be guaranteed. However, there is no reliable system available at present which allows the identity and activity of a plant based product to be measured against an accepted standard and which is universally applicable to all kinds of plant material. In one aspect, therefore, the invention as defined above represents a solution to that problem and provides a means of establishing a pharmaceutical grade standard for a therapeutic substance which is derived from, or consists of, a plant material. In this aspect the process comprises:

(i) preparing a test solution or test extract of a sample of the said therapeutic substance which is known to be of the desired pharmaceutical grade;

(ii) submitting the test solution or extract to two or more analytical methods including (a) NMR spectroscopy combined with a computer-based pattern recognition technique, and (b) one or more biological profiling techniques;

(iii) obtaining results from the analytical methods in step (ii); and (iv) defining the pharmaceutical grade standard specification on the basis of the results obtained in step (iii).

The invention further provides a process for producing a pharmaceutical grade therapeutic substance which is derived from, or consists of, a plant material, the process comprising;

(i') preparing a test solution or test extract of a candidate sample of the therapeutic substance;

(ii') submitting the said solution or extract to analysis by a combination of NMR spectroscopy and a computer-based pattern recognition technique;

(iii') obtaining results from the analysis of step (ii'); and (iv') selecting the therapeutic substance as being of pharmaceutical if the results obtained in step (iii') comply with the specification for the pharmaceutical grade standard established in step (iv) above.

When the candidate sample is selected for submission to biological profiling in addition to the NMR spectroscopic and pattern recognition analysis the above step (iv') is replaced by the following steps:

(iv'a) submitting the solution or extract prepared in step (i') to one or more biological profiling techniques;

(iv'b) obtaining results from the or each technique used in step (iv'a); and (iv'c) selecting the therapeutic substance as being of pharmaceutical grade if the results obtained in steps (iii') and (iv'b) comply with the specification for the pharmaceutical grade standard established in step (iv) of the process above.

In these embodiments the NMR spectroscopy, pattern recognition and biological profiling may all be performed as described earlier in the specification.

The invention will be further illustrated in the following Examples with reference to the accompanying Figures, in which:

FIG. 1 is a principal component analysis (PCA) score plot of factor 3 (y axis) against factor 2 (x axis) for six samples of *Panax ginseng* obtained from different suppliers as described in Example 1. The symbols used in the figure are as follows: *=supplier 1, •=supplier 2; +=supplier 3; ∇=supplier 4; □=supplier 5; and (x)=supplier 6.

FIG. 2 shows two HPLC chromatograms for Kemmun tea, using a system optimised for the separation of catechins as described in Comparative Example 1, in which A represents an untreated tea sample and B represents a tea sample which has been previously treated by passage through a solid phase extraction column.

FIG. 3 shows two HPLC chromatograms for Lapsang Souchong tea, using a system optimised for the separation of catechins as described in Comparative Example 1, in which A represents an untreated tea sample and B represents a tea sample which has been previously treated by passage through a solid phase extraction column.

FIGS. 4A and 4B are PCA score plots of factor 2 (yaxis) against factor 1 (x axis) for six different types of tea, obtained in Example 2 which follows. The symbols used in the figure for each type of tea are as follows: □=Oolong; +=Kemmun; ∇=Lapsang Souchong; •=Darjeeling; *=Gunpowder; ♦=Assam.

Figure 5:
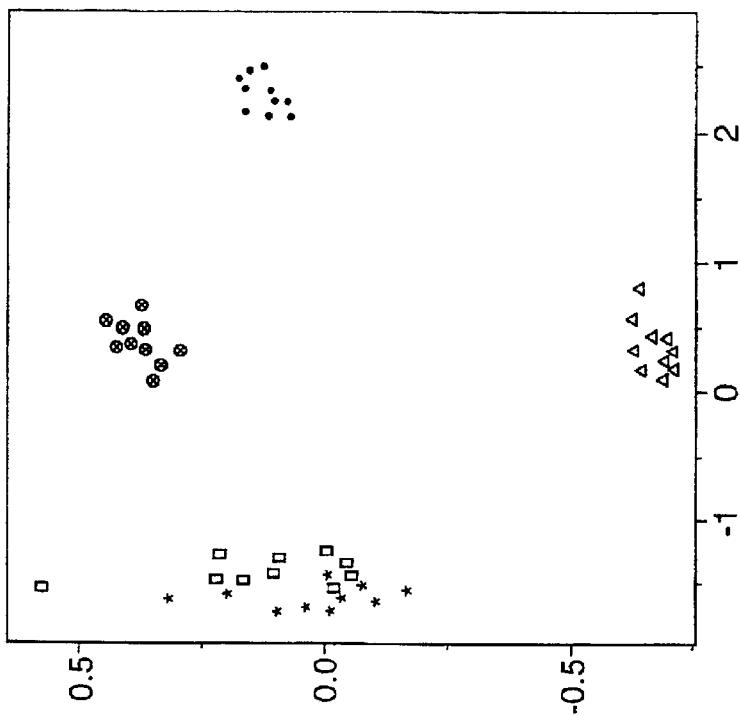

FIG. 5 is a PCA score plot of factor 3 (y axis) against factor 1 (x axis) for the five different commercial samples of *Tanacetum parthenium* (feverfew) capsules obtained in Example 3. The symbols used for each sample are as follows: (x)=sample 1; *=sample 2; □=sample 3; •=sample 4; and ∇=sample 5.

Figure 6:
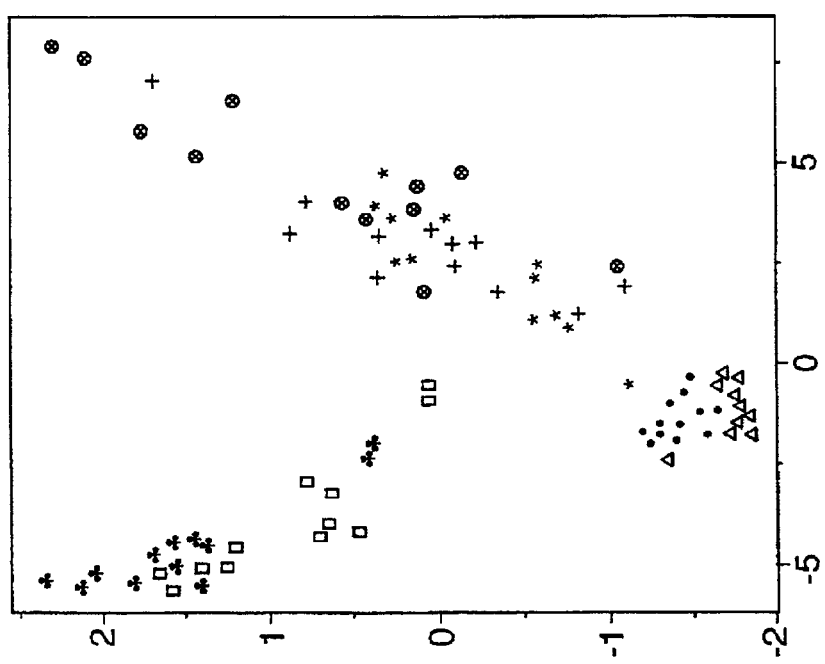

FIG. 6 is a PCA score plot of factor 2 (y axis) against factor 1 (x axis) for the seven samples of *Tanacetum parthenium* harvested at different intervals after planting out, as described in Example 4. The symbols used are as follows: •=sample T0; ∇=sample T1; (x)=sample T2; *=sample T3; +=sample T4; □=sample T5; and ♣=sample T6.

Figure 7:
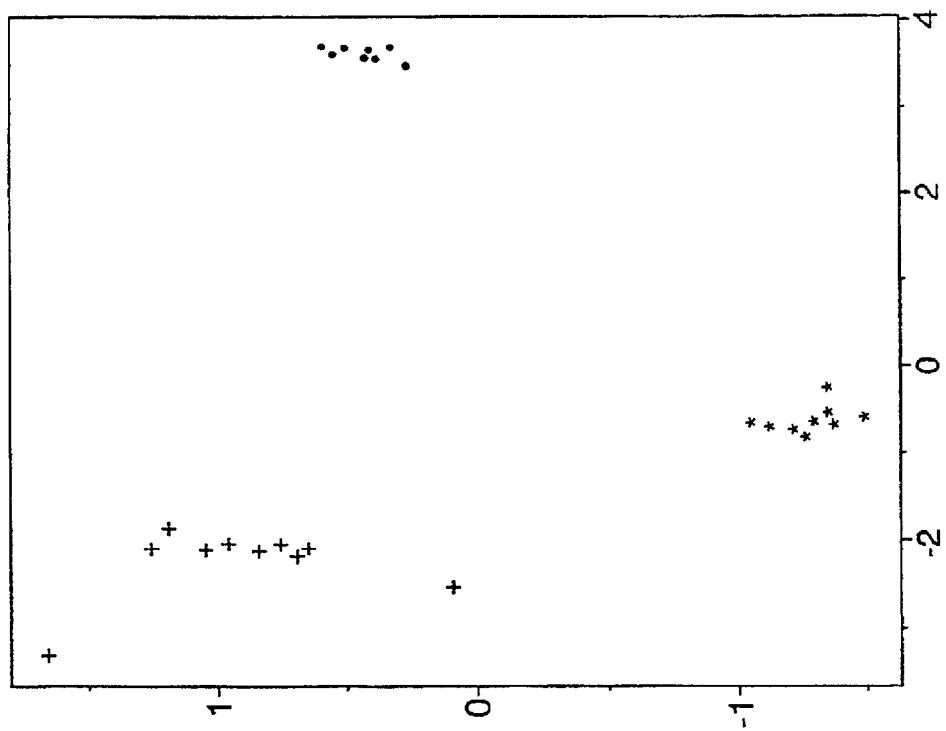

FIG. 7 is a PCA score plot of factor 2 (y axis) against factor 1 (x axis) for the Traditional Chinese Medicine remedy analysed in Example 5. The symbols used for each sample are as follows: •=supplier 1; *=supplier 2; and +=supplier 3.

Figure 8A:
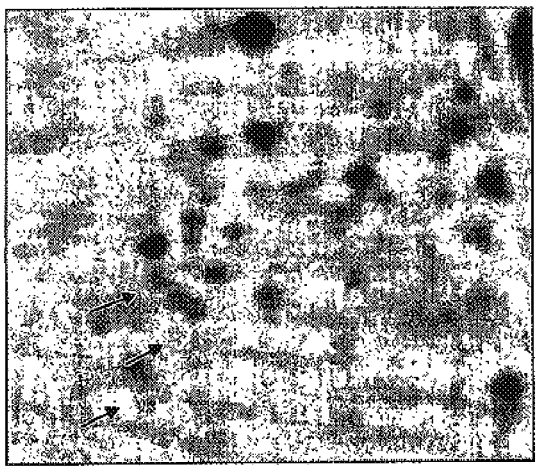
Figure 8B:
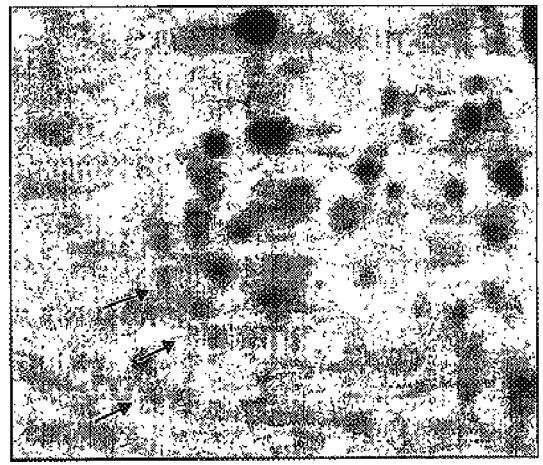

FIG. 8 is a 2-D gel protein profile (silver stain) of IBR3 human dermal fibroblasts, obtained from the assay of Example 6 which follows, wherein A is an untreated control sample and B is a sample 72 hours after treatment with a 10 μg/mL extract of *Buddleja globosa*.

Figure 9A:
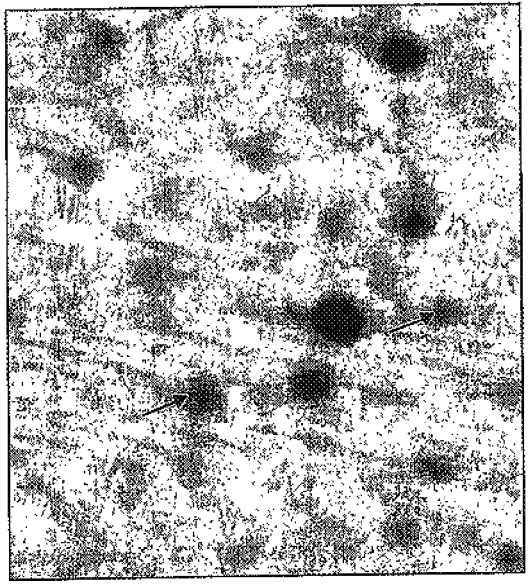
Figure 9B:
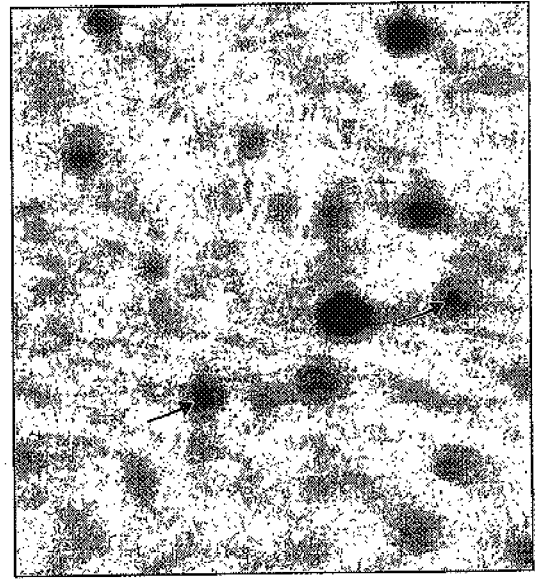

FIG. 9 is a 2D gel protein profile (silver stain) of IBR3 human dermal fibroblasts obtained from the assay of Example 6 which follows wherein A is untreated control sample and B is a sample 72 hours after treatment with a 10 μg/mL extract of *Buddleja globosa*.

EXAMPLE 1

Use of NMR Spectroscope and Multivariate Analysis to Discriminate Between Sources of *Panax ginseng*

Preparation of Extracts

Samples of white Ginseng were obtained from six different commercial suppliers. White Ginseng is derived from the root of *Panax ginseng* C. A. Meyer. The root is put in boiling water briefly and then soaked in the sugar juice. It is subsequently exposed and dried in the sun. White Ginseng is also known as Sugar Ginseng.

The dried plant root material was ground to a fine powder using an "Illico" blender for five minutes. 1 g of the powder was mixed with 20 mL of cold water and stirred continuously for 2 hours on a shaker at 150 rpm at room temperature (22° C.). The extract was filtered through Whatman No. 1 filter paper, the filtrate collected and freeze-dried overnight. 10 mg of the sample was dissolved in 1 mL of deuterated water for NMR spectroscopic analysis. 800 μL were used for NMR spectroscopic analysis and samples were referenced internally to TSP at 0.00 ppm.

Protocol for NMR Spectroscopy

Hydrogen-1 NMR spectra were recorded on a Bruker DRX 600 Spectrometer operating at 600.13 MHz for the proton frequency, fitted with a BEST flow probe. Spectra were a result of 64 scans of 20 ppm sweep width and were collected into 49152 data points. Acquisition time per scan was 2.0 seconds. Prior to transformation, a line broadening of 0.3 Hz was applied and the spectra were Fourier transformed. Referencing was to TSP at 0.00 ppm. NMR spectra were analysed using AMIX software to reduce the spectra into "histograms" containing buckets of 0.4 ppm width.

Principal Component Analysis

The resulting file was opened in Excel where normalisation was performed using the sum of the entire spectrum. The data resulting from this was then subjected to multivariate analysis using the Pirouette software package. Unsupervised PCA was performed using mean centring (and autoscaling).

Results

Figure 1:
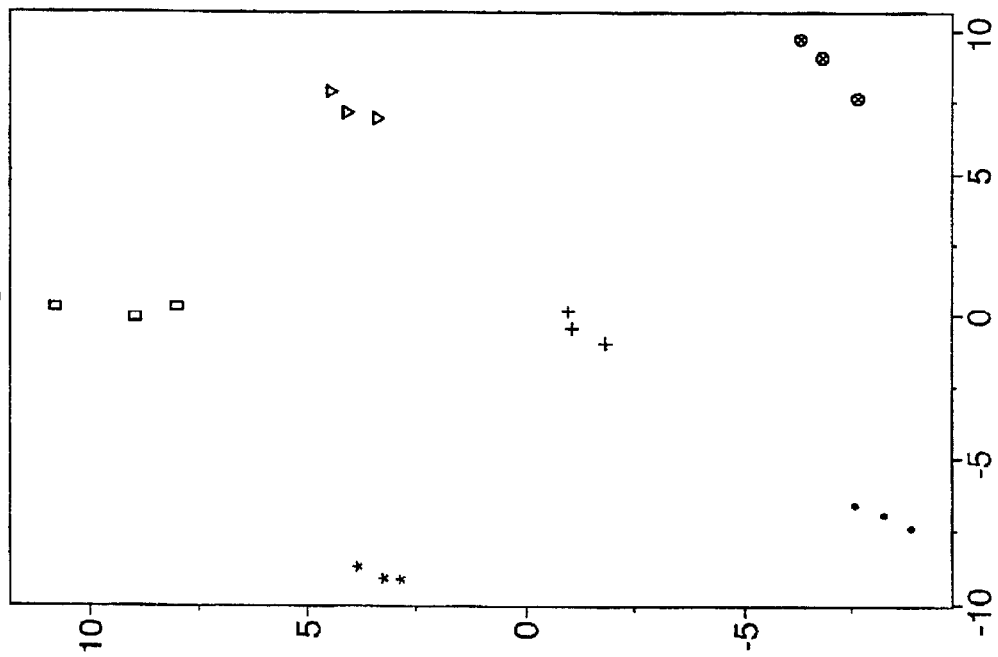

The data were converted into points on a PCA score plot. This is FIG. 1 attached. The figure clearly shows six distinct clusters of points attributable to each of the *Panax ginseng* samples, thereby illustrating that the technique provides a means of discrimination between ostensibly identical samples of a given plant material.

Comparative Example 1

HPLC Analysis of Extracts of Tea

The teas used were Kemmun and Lapsang Souchong. Extracts of each for HPLC analysis were prepared as follows:

Untreated Samples

Dried commercial tea sample (50 g) was ground to a fine powder for approximately 1 minute using a Moulinex "Illico' blender, to produce a homogeneous sample. 5 g of the powder was removed and placed in a 100 mL glass conical flask at room temperature (22° C.). 50 mL of boiling distilled water was poured over the tea sample which was stirred with a plastic rod and left at room temperature for 30 minutes. The extract was filtered through a Whatman No. 1 filter paper, the filtrate collected and freeze dried overnight. 10 mg of the sample were dissolved in 1 mL of distilled water.

HPLC equipment: Hewlett Packard series II 1090 Liquid Chromatograph

HPLC column: C18 RP Hypersil 5μ, 150×4.6 mm

HPLC mobile phase: Methanol:Water:Orthophosphoric acid 20:79.9:0.1 v/v, flow rate 0.9 ml/minute, absorption wavelength 210 nm.

The resulting chromatograms are accompanying FIGS. 2A (Kemmun) and 3A (Lapsang Souchong).

Treated Samples

Dried sea sample (50 g) was ground to a fine powder for approximately 1 minute using a Moulinex "Illico" blender, to produce a homogenous sample, 50 mL of boiling distilled water was poured over the tea sample which was stirred with a plastic rod and left at room temperature for 30 minutes. The extract was filtered through a Whatman No. 1 filter paper, the filtrate collected and freeze dried overnight. 10 mg of the sample was dissolved in 1 mL of distilled water which was run through a Reverse Phase (RP) C18 Isolute$^R$ column under vacuum. 20 μL were used for the HPLC analysis, following the method described above for the untreated samples.

The resulting chromatograms are accompanying FIGS. 2B (Kemmun) and 3B (Lapsang Souchong). The Figures show that HPLC does not clearly distinguish between treated and untreated samples of tea since chromatograms 2A and 2B are virtually identical, as are chromatograms 3A and 3B. The Figures also show that HPLC does not have the power to discriminate between different types of tea since the chromatograms of FIG. 2 are virtually identical to those of FIG. 3.

EXAMPLE 2

Use of NMR Spectroscopy and Multivariate Analysis to Discriminate Between Types of Tea The teas used were Gunpowder, Darjeeling, Kemmun, Assam, Lapsang Souchong and Oolong. Untreated and treated samples of these teas were prepared as described in Comparative Example 1.

Protocol for NMR Spectroscopy and Principal Component Analysis

The 10 mg tea samples were dissolved in 1 mL of deuterated water ($D_2O$). 800 μL were used for NMR spectroscopic analysis and samples were referenced internally to TSP at 0.00 ppm. The procedure described in Example 1 was carried out on each of the tea extracts.

Results

The data were converted into points on two score plots. These are FIGS. 4A and 4B attached. FIG. 4B shows six distinct clusters of points attributable to each of the tea extracts following treatment, whilst FIG. 4A shows that before treatment clustering was poor.

The discriminating power of the NMR spectroscopy/PCA technique is demonstrated, contrasting strongly with the inability of HPLC to distinguish tea types as shown in Comparative Example 1.

EXAMPLE 3

Use of NMR Spectroscopy and Multivariate Analysis to Discriminate Between Commercial Samples of a Herbal Remedy Preparation of Extracts Commercially available capsules of feverfew (*Tanacetum parthenium*) were obtained from three different manufacturers. The products were ostensibly identical, being hard gelatin capsules containing a 'standardised' feverfew powder.

Five samples, each consisting of 10 capsules were taken. One sample was taken from manufacturer A. Two samples, each bearing the same batch number, were taken from manufacturer B. Two samples, each bearing a different batch number, were from manufacturer 3.

| Sample No. | Manufacturer | Batch No. | Capsule content |
|---|---|---|---|
| 1 | A | I | 500 mg |
| 2 | B | II | 384 mg |
| 3 | B | II | 384 mg |
| 4 | C | III | 380 mg |
| 5 | C | IV | 380 mg |

The capsule contents from each sample were placed in a Moulinex "Illico" blender and the material ground to a fine powder for two minutes to produce a homogeneous sample. Water extracts were prepared for NMR spectroscopic analysis by dissolving 500 mg of the powder in 50 mL cold water and stirring the extract for four hours on a shaker at 150 rpm at room temperature (22° C.). The extract was filtered through Whatman No. 1 filter paper, the filtrate collected and freeze dried overnight.

Protocol for NMR Spectroscopy and Principal Component Analysis

The procedure described in Example 1 was carried out on each extract.

Results

The data were converted into points on a score plot (mean-centred). This is FIG. 5 attached, in which each point corresponds to one capsule. The plot shows that samples 1, 4 and 5 gave good clustering that reflects consistency between individual capsules in those batches of products. Samples 2 and 3 gave poorer clustering, reflecting greater variability in those particular products from capsule to capsule. The plot also highlights distinct differences between different batches of one product from one manufacturer (samples 4 and 5) which are claimed to be identical.

EXAMPLE 4

Use of NMR Spectroscopy and Principal Component Analysis to Discriminate Between Samples of *Tanacetum parthenium* of Differing Maturity Cultivation and Harvesting of Plant Samples The medicinal plant species *Tanacetum parthenium* (Feverfew) was grown in the UK from warranted seed obtained from C. N. Seeds, Ely, UK. Seeds were sown on 18$^{th}$ April and raised under glass. Plantlets emerged on 25$^{th}$ April and were planted out on 24$^{th}$ May in plots laid out on a grid basis to provide a randomised sampling regime.

Five samples consisting of 4 plants each were harvested from the plots for analysis at different intervals after planting out. Two additional samples were taken at final harvesting, stored frozen and analysed at one and two month intervals post-harvest. The dates of harvesting of the samples were as follows:

| Sample No | Date of harvesting |
|---|---|
| T0 | 30 Jun. |
| T1 | 14 Jul. |
| T2 | 4 Aug. |
| T3 | 19 Aug. |
| T4 | 18 Sep. |
| T5 | 18 Sep. and stored to 13 Oct. |
| T6 | 18 Sep. and stored to 10 Nov. |

Preparation of Extracts

Dried plant material was collected and immediately placed in a freezer at −20° C. After freezing, the material was placed in a freeze drier for 12 hours after which samples were checked to ensure they were dry. The material was placed in a Moulinex "Illico" blender, and the material ground to a fine powder for two minutes to produce a homogeneous sample. Water extracts were prepared for NMR spectroscopic analysis by dissolving 500 mg of plant material in 50 mL cold water and stirring the extract for four hours on a shaker at 150 rpm at room temperature (22° C.). The extract was filtered through Whatman No. 1 filter paper, the filtrate collected and freeze dried overnight.

Protocol for NMR Spectroscopy and Principal Component Analysis 10 mg of the sample as described above was dissolved in 1 mL of deuterated water for NMR spectroscopic analysis. 800 $\mu$L were used for NMR spectroscopic analysis and samples were referenced internally to TSP at 0.00 ppm. The procedure described in Example 1 was followed.

Results

The data were converted into points on a PCA score plot (mean-centred). This is FIG. 6 attached. There is a clear clustering of points relating to the different samples. The results demonstrate that metabolic changes in a plant, for instance as manifested int the maturing process, can be represented on a PCA map. The process of the invention thus provides a means of discriminating between samples of a given plant material having different physiological states, in this case of differing maturity levels.

EXAMPLE 5

Use of NMR Spectroscopy and Multivariate Analysis to Distinguish Between Samples of a Mixture of Plant Materials The Traditional Chinese Medicine remedy known as Liu Wei Huang Wan, which contains six plant ingredients, was obtained from three different suppliers (denoted 1, 2 and 3).

Preparation of Extracts 100 tablets from each supplier were separated into groups of 10 and weighed. They were then crushed with a pestle and mortar and 1 g of the resulting powder was transferred to a glass flask. Cold water (100 mL) was then poured over the powder and the mixture was refluxed for 30 minutes. The solution was cooled, filtered and freeze dried.

NMR Spectroscopy and Principal Component Analysis 10 mg of each sample prepared as described above was removed and dissolved in 1 mL of deuterated water. The procedure described in Example 1 was carried out.

Results

The data were converted into points on a PCA score plot (mean-centred). This is FIG. 7 attached. There is a clear clustering of points corresponding to samples from the three suppliers. These results demonstrate that the process of the invention can successfully discriminate between samples of multi-component plant materials which are ostensibly identical.

Reference Example 1

Preparation of test Extract of Buddleja spp and determination of the effect of *Buddleja globosa* on Human Dermal Fibroblast Growth

*Buddleja globosa* is a plant reported to possess wound healing properties, for which it has been used clinically in the practice of herbal medicine. In order to confirm that the plant possesses a biological activity relevant to this use, thereby justifying the choice of it as a candidate for the proteomics analysis used in Example 6, an assay to determine whether it could stimulate cell growth in vitro was carried out as described by Hughes and Cherry (1997) in Wound Repair and Regeneration 5: 159–167. For comparative purposes a different species of the same plant genus (*Buddleja davidii*), to which wound healing properties have to a lesser extent been attributed, was also tested. Grass was used as a control.
Preparation of Exacts Fresh leaves (50 g) of *Buddleja globosa, Buddleja davidii* and grass were heated separately for one hour under reflux in one liter of distilled water. The extract was cooled, filtered through a Whatman No.1 filter and the filtrate collected and freeze dried for 12 hours. Dried extract, (10 mg), was dissolved in water (1 mL) and filtered through a $0.2\mu$ filter. The extract was diluted 1:1000 into Dulbecco's Modified Eagle Medium (DMEM) media to produce a solution with a final concentration of 10 $\mu$g/ml. This solution was diluted 1:1 with DMEM to produce a 5 mg/ml solution.
Human Dermal Fibroblast Assay Human dermal fibroblasts, (HDfs), derived from post auricular surgery, were cultured at 37° C. in 5% $CO_2$ in Dulbeccos Modified Eagle Medium (DMEM), supplemented with 10% Fetal Calf Serum (FCS), 0.02% fungizone and 1% penicillin and 2% streptomycin. HDfs were grown to confluence for 1–5 days and were removed from the culture flask using 0.025% trypsin/EDTA after washing with Phosphate Buffered Saline (PBS). HDfs were decanted into a 50 mL sterile universal and re-suspended in 50 mls of DMEM after which they were centrifuged at 2700 rpm for 5 minutes. HDfs were re-suspended in 10 mLs of DMEM and counted using a haemocytometer. HDfs were seeded in DMEM containing 10% FBS into the plate 24 hours prior to use in the assay. A seeding density of $4\times10^3$ cells/microtitre well used in the assay.

The medium was removed by aspiration 24 hours later. The *Buddleja globosa* extract was initially dissolved in water at a concentration of 10 mg/ml then diluted into DMEM containing 0.5% PCS (0.5% FCS is the maintenance level for HF growth, 10% is stimulatory) at final concentrations of 5, 10 and 100 $\mu$g/ml, (n=8 for control and treatments).

Extracts were added to the plate in 200 $\mu$L of medium after filtration through a $0.2\mu$ sterile filter. Cells remained in contact with the extracts for 24 and 72 hours after addition of the Buddleja extract. They were collected at these two time points at each of the above three different concentrations. They were analysed using the Neutral Red assay described below.
Neutral Red Assay 1.2 mL of Neutral Red dye were added to 78.8 mL of Hanks' Balanced Salt Solution (HBSS). This was incubated for 10 minutes at 37° C. after which it was centrifuged at 2600 rpm for 5 minutes. 100 $\mu$L were added to each well and the plates were incubated for 2.5 hours after which the medium was decanted and the cells washed firstly with 100 $\mu$L of 1% formic acid followed by 100 $\mu$L of 1% acetic acid. The microtitre plate was placed on an AnthosHill plate reader, shaken for 15 seconds and the absorbance of the residual cells was read at 550 nm. Percentage growth was determined by comparing the absorbance values (which are converted to percentage growth) of the cells plus extract with those of the control (0.5%).
Results

TABLE

The effects of plant extracts on IBR3 human dermal fibroblast (HDf) growth.

| | Absorbance @ 550 nm | | |
|---|---|---|---|
| | Day 1 | Day 2 | Day 3 |
| 5 $\mu$g/mL | | | |
| Buddleja globosa #1 | 0.118 | 0.14 | 0.18 |
| Buddleja globosa #2 | 0.115 | 0.168 | 0.19 |
| Buddleja davidii | 0.13 | 0.137 | 0.19 |
| Grass | 0.135 | 0.14 | 0.2 |
| 0.5% FCS | 0.18 | 0.21 | 0.24 |
| 10% FCS | 0.21 | 0.3 | 0.32 |
| 10 $\mu$g/mL | | | |
| Buddleja globosa #1 | 0.235 | 0.25 | 0.26 |
| Buddleja globosa #2 | 0.115 | 0.165 | 0.17 |
| Buddleja davidii | 0.14 | 0.182 | 0.2 |
| Grass | 0.14 | 0.151 | 0.19 |
| 0.5% FCS | 0.18 | 0.21 | 0.24 |
| 10% FCS | 0.21 | 0.3 | 0.32 |
| 100 $\mu$g/mL | | | |
| Buddleja globosa #1 | 0.14 | 0.142 | 0.142 |
| Buddleja globosa #2 | 0.148 | 0.151 | 0.125 |
| Buddleja davidii | 0.12 | 0.1 | 0.15 |
| Grass | 0.138 | 0.18 | 0.21 |
| 0.5% FCS | 0.18 | 0.21 | 0.24 |
| 10% FCS | 0.21 | 0.3 | 0.32 |

These results demonstrate that *Buddleja globosa* shows a stimulatory effect on the growth of human dermal fibroblast cells at a medium concentration of 5 $\mu$g/ml and 10 $\mu$g/ml and a lesser effect at 100 $\mu$g/ml. The effect was seen to be maintained over 72 hours. The effect at the lower concentrations was reproducible since two different extracts of the same plant species gave comparable results. In contrast, *Buddleja davidii* was shown to have an inferior effect. The activity is thus species-dependent, confirming the value of ethno-botanical anecdotal information in selecting likely candidates for plant extract development. The control, grass, had a considerably reduced effect.

Since *Buddleja globosa* is effective in promoting the growth of human fibroblasts it is a suitable candidate plant extract to model the protein analysis technique described in Example 6 which follows. The results of this in vitro assay also validate the selection of IBR3 HDf as an appropriate target cell line for the protein analysis.

EXAMPLE 6

Proteomic Analysis of the Effect of *Buddleja globosa* on Protein Expression in Human Dermal Fibroblast Cells Materials and Method
Cell Culture IBR3 human dermal fibroblasts were cultured in DMEM+ 10% FCS (Sigma) using T&5 flasks (TPP plastics). Approximately 50 mg of a dried extract of *Buddleja globosa* was dissolved in 5 mL double distilled $H_2O$ to create a 10 mg/mL stock solution. The stock solution was filtered through a 0.2 µm filter and 5 µL was diluted in 5 mL DMEM+10% FCS (i.e. 1:1000dilution) to give a 10 µg/mL solution. This was diluted 1:1 in DMEM+10% FCS to give a 5 µg/mL solution.

One T75 flask was used for each of the following extract test concentrations: 0 µg/mL, 5 µg/mL, 10 µg/mL and cells were incubated for 24 hours or 3 days (total number of flasks=6).

A six-well plate (Costar) was employed for radiolabelled cultures and 2 wells per extract concentration (0 µg/mL, 5 µg/mL, 10 µg/mL) were used. [$^{35}$S]-labelled methionine, 250 µCi per well, was added to methionine-free media and the cells were incubated for 24 hours. All incubations were carried out in a $CO_2$ incubator at 37° C.

2-D Electrophoresis

Following incubation, cells in the T75 flasks were washed with 2×5 mL PBS and 1×5 mL 0.35 sucrose and collected into 200 µL lysis buffer (9.5 M urea, 1% DTT, 2% CHAPS, 0.8% Pharmalyte pH 3–10 [Pharmacia]). Cells in each well of the 6-well plate were washed with 2×2 mL PBS, 1×2 mL 0.35 M sucrose and collected into 35 µL lysis buffer. All samples were stored at −20° C. until used.

Protein concentrations were determined using a modified Bradford assay and radioactivity was determined by scintillation counting. It was necessary to perform an acetone precipitation with the unlabelled cells due to low amounts of protein. Following this step, protein concentrations were within assay parameters and permitted an accurate loading of sample.

Isoelectric Focusing

Fifty micrograms of unlabelled protein of 1×10$^6$ CPM labelled protein was added to reselling solution (8 M urea, 0.5% CHAPS, 0.2% Pharmalyte pH 3–10 [Pharmacia]) to a final volume of 450 µL and used to reswell immobilised pH gradient (IPG) strips (i.e. in-gel dehydration). For each extract condition, IPG strips covering the ranges pH 3–10 NL (non-linear) and pH 4–7 L (linear) were used. Following overnight reswelling, the IPGs were focussed for 60 kVhrs at 0.05 mA/strip, 20° C.

2-D Electrophoresis

Before the focussed IPGs were run in the second dimension, the strips were prepared for 2-D by equilibrating in buffer (1.5 m Tris [pH 8.8], 6 M urea, 30% glycerol, 2% SDS, 0.01% bromophenol blue) containing 1% dithiothreitol (DTT) for 15 minutes, followed by another 15 minutes in buffer containing 4.8% iodoacetamide (IAA).

SDS-PAGE was performed overnight (20 mA/gel, 10° C.) using 12% T/2.6%C separating gels in a Hoefer DALT system.

Visualisation

Once the second dimension had been run gels were placed into a protein fixing solution (50%, methanol, 10% acetic acid) overnight and strained using a silver straining kit (Daiichi) the following day. Radioactive gels were similarly fixed but not silver stained and placed in a "gel-drying" solution (3% glycerol, 30% methanol) overnight. The gels were then dried-down onto 3 MM paper (Whatman) using a Savant gel dryer and exposed to BioMax film (Kodak) for a total of 10 days. The films were developed in an AGFA processing machine.

After silver-staining or film development the gels and films were scanned at 100 µm resolution using a Molecular Dynamics Personal Densitometer SI and the images were viewed using ImageQuant (Molecular Dynamics). Computer analysis was performed using PDQuest (Bio-Rad) which facilitates the alignment, landmarking, matching and subsequent quantitative analysis of the images.

24 hr time point:
  (1) Cells radiolabelled with 250 µCi [$^{35}$S]-methionine
  (2) Unlabelled cells for silver staining (2×75 cm$^2$ flasks for each sample).

72 hour time point:
  (1) Unlabelled cells for silver staining (2×75 cm$^2$ flasks for each sample).

2-DE: First dimension:
  IPG strips covering two different pH ranges were used
  (1) pH 3–10 NL strips
  (2) pH 4–7 strips.

Second dimension:
  12% SDS-PAGE

Sample loading:
  50 µg protein for silver staining
  10$^6$ cpm for autoradiography Results The effect of the *Buddleja globosa* extract on protein expression by the human dermal fibroblasts is shown in the following Table:

| *Buddleja globosa* extract (µg/mL) | 24 hours spots increased >2-fold | 24 hours spots decreased >2-fold | 3 days spots increased >2-fold | 3-days spots decreased >2-fold |
| --- | --- | --- | --- | --- |
| 5 | 19 | 24 | 31 | 39 |
| 10 | 33 | 51 | 39 | 32 |

Total number of protein spots matched: 850

The accompanying FIGS. 8 and 9 show examples of protein spots showing altered patterns of expression in response to the *Buddleja globosa* extract. FIG. 8 illustrates a region where proteins are decreased following treatment with the 10 µg/mL extract after 72 hours whilst FIG. 9 illustrates a region where proteins are increased following treatment with the 10 µg/ml extract after 72 hours. In each FIG. A represents an untreated control and B represents the treated sample The results demonstrate that the technique of protein analysis can be used to confirm the presence of a relevant biological activity in a concentration-dependent manner. *Buddleja globosa* was shown in this context to be effective in altering protein expression in Human Dermal Fibroblast cells.

What is claimed is:

1. A process of establishing a standard specification for a medicinal plant material, the process comprising:
  (i) selecting a sample of the medicinal plant material, which sample is known to possess a particular desired property, as a standard sample;
  (ii) preparing a test solution or test extract of said standard sample;
  (iii) submitting said solution or extract to two or more analytical methods including (a) a combination of NMR spectroscopy and computer-based pattern recognition, said combination comprising submitting the solution or extract to NMR spectroscopy, recording one or more NMR spectra and submitting data obtained from the or each NMR spectrum to a multivariate analysis, and (b) one or more biological profiling techniques which provide a quantifiable measure of the biological effect of the plant and which include proteomics;

(iv) obtaining results from the analytical methods used in step (iii); and (v) defining a standard specification for the said plant material on the basis of the results obtained in step (iv);

the process being conducted such that the NMR data submitted to the multivariate analysis reflect the totality of the compounds in the plant material which respond to the NMR technique being used.

2. A process of providing a desired sample of a medicinal plant material, which sample complies with the standard specification for that material defined by the process of claim 1, the process comprising:

(i') preparing a test solution or test extract of a candidate sample of the medicinal plant material;

(ii') submitting said solution or extract to two or more analytical methods including (a) combination of NMR spectroscopy and a computer-based pattern recognition, said combination comprising submitting the solution or extract to NMR spectroscopy, recording one or more NMR spectra and submitting data obtained from the or each NMR spectrum to a multivariate analysis, and (b) one or more biological profiling techniques which provide a quantifiable measure of the biological effect of the plant and which include proteomics;

(iii') obtaining results from the analysis of step (ii');

(iv') selecting the candidate sample if the results in step (iii') comply with the standard specification for the said material established in step (iv) of the process defined in claim 1;

the process being conducted such that the NMR data submitted to the multivariate analysis reflect the totality of the compounds in the plant material which respond to the NMR technique being used.

3. The process according to claim 1, which further comprises representing the results of the multivariate analysis as one or more points on a score plot.

4. The process according to claim 1 wherein the multivariate analysis is principal component analysis (PCA).

5. The process according to claim 1 wherein the proteomics analysis comprises:

(i) providing a target cell selected according to the clinical indication in which the medicinal plant is active and incubating the target cells with the test solution or test extract; and (ii) subjecting the incubated cells to gel electrophoresis on a 2-D gel and observing the change in protein expression in the cells as a result of exposure to the said solution or extract.

6. The process according to claim 1 wherein the medicinal plant material consists of, or is derived from, a whole plant, a part of a plant, a plant extract or a plant fraction.

7. The process according to claim 1 wherein the standard sample is a sample of authenticated or audited plant material of which the provenance is known.

8. A process of establishing a standard specification for a medicinal plant material, the process comprising:

(i") selecting a sample of the medicinal plant material, which is known to possess a particular desired property, as a standard sample;

(ii") preparing a test solution or test extract of said standard sample;

(iii") submitting the test solution or test extract to NMR spectroscopy and recording one or more spectra;

(iv") submitting the data obtained from the or each said NMR spectrum, those data reflecting the totality of the compounds in the plant material which respond to the NMR technique being used, to a multivariate analysis to generate one or more points on a score plot; and (v") defining a sphere of acceptability around the points generated in step (iv") as the, or as part of the, standard specification for said plant material.

9. The process according to claim 8 wherein the multivariate analysis of step (iv") is performed using an unsupervised methodology.

10. A process of providing a desired sample of a medicinal plant material, which sample complies with the standard specification for that material defined by the process of claim 9, the process comprising:

(i''') preparing a test solution or test extract of a candidate sample of said plant material;

(ii''') submitting the test solution or test extract to NMR spectroscopy and recording one or more spectra;

(iii''') submitting the data obtained from the or each said NMR spectrum, reflecting the totality of the compounds in the plant material which respond to the NMR technique being used, to a multivariate analysis to generate one or more points on a score plot; and (iv''') selecting the candidate sample as said desired sample which complies with said standard specification only if the points generated on the score plot in step (iii''') fall within the sphere of acceptability as defined in step (v") of the process of claim 9.

11. The process according to claim 1 or 8 wherein the plant material is derived from, or consists of, a mixture of two or more different plants.

12. The process according to claim 11 wherein the said mixture is a remedy from a system of traditional medicine where mixtures of plants or plant extracts are used.

13. The process according to claim 12 wherein the system of traditional medicine is Traditional Chinese Medicine or Ayurvedic Medicine.

14. A process of establishing a standard specification for a medicinal plant material, the process comprising:

(i) selecting a sample of the medicinal plant material, which sample is known to possess a particular desired property, as a standard sample;

(ii) preparing a test solution or test extract of said standard sample;

(iii) submitting said solution or extract to two or more analytical methods including (a) a combination of NMR spectroscopy and computer-based pattern recognition, said combination comprising submitting the solution or extract to NMR spectroscopy, recording one or more NMR spectra and submitting data obtained from the or each NMR spectrum to a multivariate analysis, and (b) one or more biological profiling techniques which provide a quantifiable measure of the biological effect of the plant and which include a proteomics, said proteomics comprising (a') providing a target cell selected according to the clinical indication in which the medicinal plant is active and incubating the target cells with the test solution or test extract; and (b') subjecting the incubated cells to get electrophoresis on a 2-D gel and observing the change in protein expression in the calls as a result of exposure to the said solution or extract;

(iv) obtaining results from the analytical methods used in step (iii); and (v) defining a standard specification for the said plant material on the basis of the results obtained in step (iv);

the process being conducted such that the NMR data submitted to the multivariate analysis reflect the totality of the compounds in the plant material which respond to the NMR technique being used.

* * * * *

UNITED STATES PATENT AND TRADEMARK OFFICE
CERTIFICATE OF CORRECTION

PATENT NO. : 6,806,090 B1  Page 1 of 1
DATED : October 19, 2004
INVENTOR(S) : Hylands et al.

It is certified that error appears in the above-identified patent and that said Letters Patent is hereby corrected as shown below:

<u>Title page,</u>
Insert Item:
-- Related U.S. Application Data
[60] Provisional application Nos. 60/120,591 filed February 18, 1999, 60/149,468 filed August 19, 1999; 60/168,382 filed December 2, 1999. --

Signed and Sealed this

Eighth Day of February, 2005

JON W. DUDAS
*Director of the United States Patent and Trademark Office*